US008476248B2

(12) United States Patent
Arigony Souto

(10) Patent No.: US 8,476,248 B2
(45) Date of Patent: Jul. 2, 2013

(54) PROCESS FOR THE PREPARATION OF A WATER-SOLUBLE COMPLEX HAVING RESVERATROL COMPOUNDS; PRODUCTS COMPRISING SAID COMPLEX; AND USES THEREOF

(75) Inventor: Andre Arigony Souto, Porto Alegre (BR)

(73) Assignees: Uniao Brasileira de Educacao e Assistencia—Mantenedora da PUCRS, Porto Alegra (BR); Eurofarma Laboratorios Ltda., Sao Paulo (BR)

( * ) Notice: Subject to any disclaimer, the term of this patent is extended or adjusted under 35 U.S.C. 154(b) by 450 days.

(21) Appl. No.: 12/670,310

(22) PCT Filed: Jul. 23, 2008

(86) PCT No.: PCT/BR2008/000216
§ 371 (c)(1),
(2), (4) Date: Apr. 1, 2010

(87) PCT Pub. No.: WO2009/012551
PCT Pub. Date: Jan. 29, 2009

(65) Prior Publication Data
US 2010/0204179 A1    Aug. 12, 2010

(30) Foreign Application Priority Data
Jul. 23, 2007    (BR) ...................................... 0705319

(51) Int. Cl.
*A61K 31/05*    (2006.01)
*A61K 31/724*   (2006.01)
*A61K 47/40*    (2006.01)

(52) U.S. Cl.
USPC ............................................ 514/58; 514/734

(58) Field of Classification Search
None
See application file for complete search history.

(56) References Cited

U.S. PATENT DOCUMENTS
6,884,885 B2 *   4/2005   Qi .................................. 536/124
2006/0292099 A1  12/2006  Milburn et al.

FOREIGN PATENT DOCUMENTS
WO    WO 2006/138418    12/2006

OTHER PUBLICATIONS

Batacche, V. et al "Host-Guest interaction study of resveratrol with natural and modified cyclodextrins" J. Incl. Phen. Macrocyclic Chem. (2006) vol. 55, pp. 279-287.*
Del Valle, E. "Cyclodextrins and their uses: a review" Proc. Biochem. (2004) vol. 39, pp. 1033-1046.*
Marier, J. et al "Metabolism and disposition of resveratrol in rats . . . " J. Pharmacol. Exp. Ther. (2002) vol. 302, No. 1, pp. 369-373.*
Loftsson, T. et al "The complexation efficiency" J. Incl. Macrocycl. Chem. (2007) vo 57, pp. 545-552.*
Lopez-Nicolas, et al. "Determinationof Stoichiometric Coefficients and Apparent Formation . . ."; Journal of Chromatography; vol. 1135 (2): 158-165; Nov. 9, 2006.
Lucas-Abellan et al. "Cyclodextrins as Resveratol Carrier System" Food Chemistry; vol. 104 (1): 39-44; Apr. 14, 2007.
Pandey, S.. et al., A Review on Pharmaceutical Application of Cyclodextrins, International Journal of Pharmacy & Technology 2 (2010) 281-319.
Brewster, E. M. and Loftsson, T, Cyclodextrins as pharmaceutical solubilizers, Advanced Drug Delivery Reviews 59 (2007) 645-666.
Loftsson, T., et al., Cyclodextrins as Functional Excipients: Methods to Enhance Complexation Efficiency, Journal of Pharmaceutical Sciences, 101, (2012) 3019-3032.

* cited by examiner

*Primary Examiner* — Leigh Maier
(74) *Attorney, Agent, or Firm* — Laurence P. Colton; Smith Risley Tempel Santos LLC

(57) ABSTRACT

The present invention provides products having resveratrol with high water solubility and nutraceutical and/or phytotherapic compositions having said substances. The processes for obtaining them include the solubility increase of the polyphenol corresponding to a resveratrol compound, preferably trans-resveratrol in water, by its complexation with cyclodextrin under specific conditions that favor thermodynamic equilibrium. The products of the invention present high solubility and purity in aqueous medium, being, therefore, useful to prepare nutraceutical compositions (pharmaceutical and/or alimentary) with antioxidant, anti-inflammatory, antiviral, antidiabetics, cardioprotective, neuroprotective, chemoprotective activities; besides protecting against infections and ischemia, reducing obesity, and preventing aging. Phytotherapic compositions useful to the same therapeutical activities, prepared from the complex of resveratrol and cyclodextrin compound, preferably beta-cyclodextrin/trans-resveratrol, are also provided.

14 Claims, 3 Drawing Sheets

US 8,476,248 B2

PROCESS FOR THE PREPARATION OF A WATER-SOLUBLE COMPLEX HAVING RESVERATROL COMPOUNDS; PRODUCTS COMPRISING SAID COMPLEX; AND USES THEREOF

FIELD OF THE INVENTION

The present invention relates to products having an improved form of resveratrol, to nutraceutical and/or pharmaceutical compositions, particularly the phytotherapic ones, having said products, and to the process for obtaining a complex of resveratrol and cyclodextrin compound with high solubility. The products of the invention present surprisingly high water solubility and, consequently, improved bioavailability.

BACKGROUND OF THE INVENTION

Resveratrol compounds, specially trans-resveratrol (3,5,4'-trihydroxystilbene), presents antioxidant, anti-inflammatory, antiviral, cardioprotective, neuroprotective, and chemoprotective activities. Besides protecting against infections and ischemia, they reduce obesity and prevent aging. Trans-resveratrol is a polyphenol found mainly in red grape skin and red wine. The more intense wine or grape color, the bigger their polyphenol content is. Studies seem to indicate that trans-resveratrol can lower levels of low-density lipoproteins, also known as LDL cholesterol or "bad" cholesterol, and increase levels of high-density lipoproteins, HDL cholesterol, or "good" cholesterol. Especially when in oxidized state, LDL can be retained in blood vessel walls resulting in the formation of atheroma plaques. These plaques cause atherosclerosis, which leads to blood vessel obstruction. Trans-resveratrol stimulates HDL production by liver, decreases LDL production and avoids circulating LDL oxidation; therefore, it plays a role in reducing the risk of cardiovascular disorders, such as myocardial infarct.

Trans-resveratrol is also widely known as a modulator of the expression and activity of a protein class called sirtuin. Sirtuin modulators are compounds that up regulate (activating or stimulating), down regulate (inhibiting or eliminating), or change the functional property or the biological activity of sirtuin protein.

Sirtuin is a member of the family of protein deacetylases (Sirtuins), or rather of the Sir2 family, which includes yeast Sir2 protein (GenBank Accession No. P53685), *C. elegans* Sir-2.1 (GenBank Accession No NP_501912), and human SIRT1 (GenBank Accession No. NM_012238 and NP_036370 or AF083106) and SIRT2 (GenBank Accession No NM_012237, NM_030593, NP_036369, $NP_{13}$ 085096, and AF083107).

Sirtuin protein modulators, such as resveratrol compounds, particularly trans-resveratrol derivatives, actuate to minimize or treat aging diseases, chronic degenerative diseases of circulatory and neurological systems, such as ocular diseases (WO 2006/127987), psychopathologies (WO 2006/138418), diabetes (WO 2006/104586), cancer (WO 2006/102557), and obesity (US 2006/111435).

However, trans-resveratrol has low water solubility, less than 0.03 g/L, which complicates its oral administration (bioavailability) and its use as additive in non-alcoholic beverages. To bypass this restriction, without the synthesis of another derivative, is used in the present invention the preparation, under specific conditions, of a complex of resveratrol compound, preferably trans-resveratrol, with a cyclodextrin, preferably beta-cyclodextrin (β-cyclodextrin), presenting substantial and surprising increase in solubility.

Cyclodextrins are cyclic oligosaccharides, also known as cycloglucans or Schardinger dextrins, produced from starch by enzymatic action. Cyclodextrins can be natural or semi-synthetic. Natural cyclodextrins are, for example, α-cyclodextrin, β-cyclodextrin and γ-cyclodextrin. The use of natural cyclodextrins as a carrier of active principles has been considered restrict due to its relatively low solubility in water, particularly when it comes to β-cyclodextrin (Uekama, K.; Hirayama, F. and Irie, T. "Cyclodextrin Drug Carrier Systems". Chem. Rev. 98(5), 2045-2076, 1998). To bypass such limitation, the semi-synthetic derivatives of β-cyclodextrin prepared by methylation or hydroxy-alkylation of the hydroxyl groups of β-cyclodextrin were obtained, resulting in amorphous cyclodextrins that are more water soluble.

Beta-cyclodextrin (β-CD) is a crystalline cyclodextrin composed of seven units of D(+)-glucopyranoses linked α-(1-4), being the most employed in food area. As for its metabolism, it is considered digestible especially in large intestine when it is fermented by bacterial flora, fact determined in animal and human experiments. β-CD is not toxic neither genotoxic, even when ingested in high concentrations (Diniz, A. C. P. et al. Cienc. Tecnol. Aliment. 2005. 25(2), 197).

Recently, it was reported that aqueous solutions of trans-resveratrol and β-CD, in a ratio of 1:1, increase resveratrol water solubility, as well as its bioavailability in model systems (López-Nicolás J. M, et al *J. Chromatogr. A*, 2006, 158; Lucas-Abellán, C. *Food Chem.*, 2007, 39 and Lucas-Abellán, C.; Fortea, I., López-Nicolás, J. M. and Núñez-Delicado, E. "Cyclodextrins as resveratrol carrier system". Food Chemistry, 104 (2007) 39-44, available online in Jan. 4, 2007). However, said document does not reveal the process for obtaining β-CD/trans-resveratrol (β-CD/Res) chemical complex, neither how obtaining it to use in formulations. In addition, the document does not specify the alleged "solubility increase", but it does mention the great influence of complexation conditions in β-cyclodextrin/resveratrol complex properties.

Bertacche et al. (Bertacche, V., Lorenzi, N., Nava, D., Pini, E. and Sinico, C. "Host-Guest Interaction Study of Resveratrol with Natural and Modified Cyclodextrins". Journal of Inclusion Phenomena and Macrocyclic Chemistry, Vol. 55 (3-4). August 2006, 279-287) revealed the use of cyclodextrin to form cyclodextrin/resveratrol complex, mentioning natural cyclodextrins (α, β or γ) or modified ones (resulting from any of these forms). However, there is no specification about relative concentrations of any of such cyclodextrins in relation to resveratrol; neither there is formation of a cyclodextrin-resveratrol crystalline complex with amazingly high solubility.

It can be concluded from scientific literature that the formation of a complex with cyclodextrin is equivalent to a reaction, that is, different parameters or process conditions result in products with different characteristics. This can be observed, for example, in the several different approaches of patent literature, described below.

Patent literature considers some documents related to processes for obtaining trans-resveratrol, highlighting some of them that cite the use of cyclodextrin. Although none of the documents discloses or even indirectly suggests the inventive concept of the present invention, some of them are mentioned below as reference.

Some patent applications show the use of cyclodextrins and trans-resveratrol as a part of pharmaceutical formulations obtained by a physical mixture with other substances, but the isolation of trans-resveratrol/β-cyclodextrin (β-CD/Res) complex does not happen.

International patent application WO 2007/009997, filed by Actimex S.r.l. (Italy) and entitled "Composition Containing Micronutrients with Improved Anti-oxidant Activity and Use Thereof", presents compositions in fine powder form having ternary mixtures. Such ternary composition has an active component, a carrier and an auxiliary co-grinding agent, since the process of obtainment include grinding for at least 90 minutes. Although in said document resveratrol is mentioned as one of the active components and cyclodextrin as one of the possible carriers, the obtainment of a β-CD/Res chemical complex with high water solubility is not shown.

United States patent application US 2006/111318, filed by Advanced Medicine Research Institute and entitled "Agent for treating eye diseases", shows an agent for treating eye diseases containing sexual steroid hormone and a sirtuin modulator, which can be resveratrol. In said document, the process for preparing eye drops includes water dissolution of resveratrol, forming a suspension, and the addition of γ-cyclodextrin and 2-hydroxypropyl-β-cyclodextrin. The increase in solubility by complexation with this cyclodextrins mixture is attributed to the use of amorphous cyclodextrins instead of crystalline cyclodextrins, such as β-cyclodextrin.

Japanese patent application JP 2000/344622, filed by Sunstar Inc. and entitled "Stabilization of Stilbenic Compound and Plant Extract Containing the same, and Food, Medicine, Cosmetic or Oral Cavity Preparation Stably Compounded with Stilbenic Compound and Plant Extract Containing the same", shows the combination of stilbenic compounds with cyclodextrin, as a way to increase stability and efficiency of stilbenic compound absorption. Although resveratrol is one of the possible stilbenic compounds in said document, the obtainment of a crystalline chemical complex of resveratrol with cyclodextrin compound with high water solubility is not revealed.

Other patent applications show the obtainment of cyclodextrin complexes with other molecules than trans-resveratrol, which, in such documents, appears only as a part of the formulation. For example, the international patent application WO 2003/077860 shows the cyclodextrin complex with 3-β-acetyl-11-keto-β-boswellic acid; WO 2004/087121, provides the obtainment of cyclodextrin complex with digitalis glycosides; and WO 2006/083458 relates to the preparation of cyclodextrin complex with diindolylmethane.

The complexation of poorly soluble compounds by cyclodextrins, in which the molecules of said compounds are "guests" in the cavity of cyclodextrin molecule, is carried out in solid medium as well as liquid medium or even in semisolid medium. Such methods have advantages and disadvantages that depend on several factors and may be cited as the most important the steric hindrance, the stability of said compounds, the presence of non-reacted components, and the crystallinity of chosen cyclodextrin.

A representative example of the difficulties to be overcome in complexation process is the obtainment of inclusion complex of piroxicam (a practically insoluble substance)-cyclodextrin. The methods known by the state of the technique include reactions that can happen in solid as well as liquid medium and even in semisolid medium.

Concerning to the complexation of piroxicam in liquid medium: (1) in EP 153998, the complexation of piroxicam with a cyclodextrin selected from α-, β-, and γ-cyclodextrin group is described. The reaction can be carried out by: (a) direct dissolution of piroxicam in an aqueous solution of selected cyclodextrin and separation of the complex by crystallization; (b) piroxicam dissolution in an organic solvent and mixture of the resulting organic solution, under stirring, with an aqueous solution of selected cyclodextrin and separation of the complex by crystallization; (c) dissolution of piroxicam and cyclodextrin compounds, under stirring, in a water-ammonia solution and separation of the complex by drying; and (d) dissolution of piroxicam and cyclodextrin compounds, under stirring, in a water-hot ammonia solution and separation of the complex by freeze-drying or atomization in air flow; (2) in WO 03105906, a complexation process is described: piroxicam and β-cyclodextrin are diluted in water in the presence of ammonium hydroxide under a temperature of 60° C., the solution being then cooled to nearly −10° C. and, afterwards, lowering the temperature of the frozen solution to at least −20° C., preferably from −30° C. to −40° C.; finally, the solution is dried under vacuum; and (3) in WO 06013039, a preparation process of a piroxicam:β-cyclodextrin (1:2.5) inclusion compound is described piroxicam and β-cyclodextrin are diluted, in a molecular ratio of 1:2.5, in hot water and in the presence of ammonium hydroxide; the resulting solution undergoes drying by spray-drying with rigorous control of input and output temperatures of the drying gas and posterior separation of the complex into powder. These different methods for obtaining the same complex (piroxicam/β-cyclodextrin) show how complicate its preparation is and aim to solve problems related to scale enlargement, from laboratory to industry, and for obtaining an amorphous type of piroxicam/β-cyclodextrin complex to improve solubility and reduce the risks of crystallization of the complex during storage.

Concerning the complexation of piroxicam in semisolid medium, document WO 03053475 presents a preparation process of inclusion complexes of an active principle (in example 1, piroxicam) and a cyclodextrin (α-, β-, γ-cyclodextrin or a semisynthetic cyclodextrin, such as hydroxypropyl-β-cyclodextrin) by mixing said active principle and cyclodextrin, both in the form of finely divided powders, in the presence of small amounts of water or alcoholic, acid or base aqueous solutions. The resulting mixture is treated in a microwave oven and the resulting product is dried under vacuum at room temperature or with heating at a temperature under 50° C. It is mentioned that the technique improvement to obtain cyclodextrin complexes relates to the obtainment of complexes that are more wettable, have a greater solubility equilibrium and a faster dissolution in aqueous medium comparing to the crystalline active principle, resulting in more auspicious pharmacokinetics and, therefore, best therapeutic results.

Finally, concerning the complexation of piroxicam in solid medium, document EP 449167 presents a preparation process of piroxicam-cyclodextrin complexes, where both compounds, in the form of finely divided powders, are mixed in solid state and grinded under high-energy conditions in a steam chamber. The resulting product is dried under vacuum and sifted to eliminate any aggregates. It is mentioned that the improvement aimed at obtaining a piroxicam-cyclodextrin complex with high density and big surface area, properties that, when combined with an extremely thin size of the particle, result in an appropriate product to pharmaceutical compositions of oral, rectal, and topical administration.

One of the methods suggested in the state of the technique to improve the stability of "guest" molecules in cyclodextrin complexes is described in WO 06137959. The method shown in said document comprises the mixture of cyclodextrin and an emulsifier, the addition to this mixture of the compound to be complexed, diluted in an appropriate solvent, to the formation of the aimed complex, and finally the addition of non-complexed cyclodextrin to the inclusion complex of cyclodextrin to form a stabilizing system of the "guest" molecule.

The teachings of WO/2005/111224 are useful to complexation technique of insoluble or slightly water soluble substances with cyclodextrins. In the examples of said document, a process for obtaining a coenzyme Q10 and β-cyclodextrin soluble in water is described. The dissolution of β-cyclodextrin in water is carried out at a temperature of 30° C., preferably between 55° C. and the boiling temperature. Coenzyme Q10 is added either in solid form or dissolved in an appropriate solvent, preferably in solid form. The stirring is carried out at increased temperature, then at room temperature for several hours. Afterwards, the complex is isolated by filtration, decantation, or water evaporation. Optionally the complex is dried.

U.S. Pat. No. 6,884,885 describes a process for preparing active principle and cyclodextrins complexes to increase the yield of the complexes. The process comprises the dissolution of cyclodextrin and guest molecule in a liquid solvent at a temperature ranging from 20° C. to 100° C., preferably from 60° C. to 80° C. Cyclodextrin should be at a concentration of about 15% (p/p) or above, and said solution should have a molecular ratio of cyclodextrin to said molecule of about 1:1 to about 10:1. Then the mixture of the solution is carried out to allow a complex to form as a precipitate. The precipitate (complex) is separated.

The teachings of the documents mentioned above show the difficulties of the complexation of insoluble or slightly water soluble active principles by cyclodextrins. There are many parameters to be controlled in the obtainment of water-soluble complexes presenting purity level appropriate to pharmaceutical or nutraceutical use, acceptable industrial yield and stability of the complex during storage of the products having them. It should be noted that several documents about the state of the art mention the fact that the presence of non-reacted raw material in the final complex can cause stability problems of the products during storage.

Although cyclodextrins can be considered interesting carriers to active principles, especially to hydrophobes, in pharmaceutical formulations the selection of appropriate cyclodextrin to a specific active principle and determination of reaction conditions to the preparation of the aimed complex are fundamental. The literature has some important contributions that help us in this significant task. For example, the advantages and physico-chemical characteristics of cyclodextrins are detailed in the work of Uekama and collaborators (1998), where it is mentioned that hydroxyalkylated cyclodextrins increase the solubility of complexes formed with hydrophobic substances due to their amorphous feature (Part III, Item A.1 ("Hydroxyalkylated Cyclodextrins")). On the other hand, Uekama et al. also show that amorphous forms are easily transformed into stable crystalline form during handling and storage of medicines, being important the control of the crystallization, of the polymorphic transition and the formation of whiskers (flexible and strong crystals), especially in correlation with cyclodextrin effect in the physical stability of active principles in solid state. Despite Uekama and co-workers remarking the differentiated performance of hydroxypropyl-β-cyclodextrin, this behavior is not the same for all the active principles, for example, when β-cyclodextrin is indicated to the production of isosorbide-5-mononitrate pills (vasodilator) to avoid whiskers (part III, Item B.2 ("In the Solid State").

Chinese patent application CN 2005/1566054, filed by Institute of Materia Medica (China) and entitled "Resveratrol oligo cattail compounds, its manufacturing process, pharmaceutical combination, and uses thereof", shows the obtainment of a cyclodextrin complex with cis-ε-viniferine, an oligomeric stilbenic compound of Veratrum album.

International patent application WO 2004/103265, filed by Enprani Co. and entitled "Whitening and Antioxidative Cosmetic Composition Containing Resveratrol and Method for Preparing the Same", describes the use of cyclodextrin (hydroxypropyl-β-cyclodextrin) and polyethyleneglycol to stabilize a cosmetic composition having trans-resveratrol. In said composition, another stabilizer is also used, selected from alpha-lipoic acid, Phellodendron extract or Alteromonas ferment extract.

Chinese patent application CN 1500479, published on Jun. 2, 2004 and entitled "Resveratrol, Piceid and its Derivative and its Preparation", describes the obtainment of hydroxypropyl-β-cyclodextrin clathrates in the ratio of 1:50. The preparation process described in said document comprises resveratrol dissolution in an organic solvent 1-5 times, hydroxypropyl-beta-cyclodextrin dissolution in distilled water 5-50 times, drip of this aqueous solution in the suspension with resveratrol, mixture agitation, filtration and freeze drying to obtain the product in the form of clathrate which is intended for injection use.

In the International patent applications WO 2006/127987 (corresponding to US 2006/0292099) and WO 2006/105403, whose applicant is Sirtris Pharmaceuticals, Inc. and entitled "Treatment of Eye Disorders with Sirtuin Modulators", ophthalmic preparations comprising inclusion complexes formed by resveratrol and cyclodextrins are described. It is mentioned that, preferably, cyclodextrins are modified to increase resveratrol solubility and, hence, its bioavailability (pages 148-150 and 159-162 from documents WO 2006/105403 and WO 2006/127987, respectively). In such documents, it was suggested the use of amorphous cyclodextrin, with a new approach to obtain the complex and surprising results in terms of increased solubility and its magnitude. It is important to note that emphasis is given to the fact that the use of cyclodextrin derivatives in amorphous form is advantageous, such as hydroxypropyl-β-cyclodextrin, because non-modified cyclodextrins (α-, β- and γ-cyclodextrin) tend to crystallize, being, therefore, less water soluble than the amorphous one. However, the disadvantages resulting from the handling of amorphous substances in pharmaceutical techniques are not mentioned, which may render some pharmaceutical forms not feasible, such as, for example, solid pharmaceutical forms such as pills. This is definitely a limiting factor in the preparation of pharmaceutical compositions, such limitation being circumvented when preparing pharmaceutical compositions with crystalline complex of resveratrol and cyclodextrin compound forms—which is one of the technical features of the present invention.

Therefore, no document found in prior art showed a concrete report or even suggestion that crystalline CD/Res complex would provides a substantial increase in resveratrol solubility and, hence, resveratrol enhanced bioavailability and, at the same time, keeping complex stability during final product handling and storage. The substantial solubility increase of the complex of the present invention, compared to the solubility of other resveratrol and cyclodextrin complexes known in the art, is surprising and circumvent several technical limitations of the currently known approaches.

SUMMARY OF THE INVENTION

In one aspect of the invention, is provided an improved nutraceutical product containing resveratrol. The complex of resveratrol and cyclodextrin compound of the invention obtained by the complexation process is characterized by presenting, at least, water solubility 100 times higher than the solubility of non-complexed resveratrol compound, purity up to 98%, preferably from 91 to 98%, and by being in crystalline form.

In a preferential aspect of the invention, being, therefore, other of its objects, an improved process to obtain a soluble complex of trans-resveratrol and/or its derivatives in aqueous medium is provided, increasing its bioavailability and/or stability. The process of the invention comprises the following steps: (i) dissolution of appropriate cyclodextrin in water, in a concentration equivalent to the saturation limit, with heating from 50 to 80° C. for a sufficient time to complete its dissolution; (ii) adding, to the resulting solution, a water miscible and physiologically acceptable organic solvent to an organic solvent:water ratio ranging from 1:1 to 1:5; (iii) adding, to the mixture resulting from stage (ii), a solution of a resveratrol compound diluted in an water miscible and physiologically acceptable organic solvent, heating the resulting mixture at a temperature ranging from 50 to 80° C. for a sufficient time to complete its dissolution; (iv) cooling the resulting solution from stage (iii) until precipitation of crystals from the complex of resveratrol/cyclodextrin compound; and (v) separation of crystals from the complex of resveratrol/cyclodextrin compound, preferably by filtration under reduced pressure.

Another aspect of the invention is to provide a water-soluble resveratrol-rich phytotherapic composition, said composition having the soluble complex of resveratrol and cyclodextrin compound of the invention and a pharmaceutically acceptable carrier.

In other aspect of the invention being therefore other of its objects, a water-soluble resveratrol-rich medicine is provided, said medicine comprising a composition having the soluble complex of resveratrol and cyclodextrin compound of the invention and a pharmaceutically acceptable carrier.

In other aspect of the invention being therefore other of its objects, a water-soluble resveratrol-rich functional food is provided, said food comprising a composition having the soluble complex of resveratrol and cyclodextrin compound of the invention and a nutraceutically acceptable carrier. Said functional food comprises juices, nectars, isotonics or mixtures thereof.

In a preferential aspect of the invention, resveratrol compound is high water-soluble trans-resveratrol, being obtained, according to the invention process, in appreciable amounts and with high level of purity, enabling its direct inclusion in nutraceutical compositions. Trans-resveratrol presents antioxidant, anti-inflammatory, antiviral, cardioprotective, neuroprotective, chemoprotective activities. Besides protecting against infections and ischemia, it reduces obesity and prevents aging.

The present invention comes to fill a gap in the state of the art by providing a unique process for obtaining the complex of resveratrol and cyclodextrin compound, preferably β-cyclodextrin/trans-resveratrol, with high level of purity. The complex of the invention increases substantially the solubility of resveratrol compound, for example, trans-resveratrol in aqueous medium.

The product obtained by the process of the invention is an improved active principle that, when included in nutraceutical compositions, provides antioxidant, anti-inflammatory, antiviral, antidiabetics, cardioprotective, neuroprotective, chemoprotective action, besides protecting against infections and ischemia, reducing obesity, and preventing aging.

These and other objects of the present invention will be understood and appreciated from the detailed description of the invention and its claims attached.

DETAILED DESCRIPTION OF THE INVENTION

Figure 1:
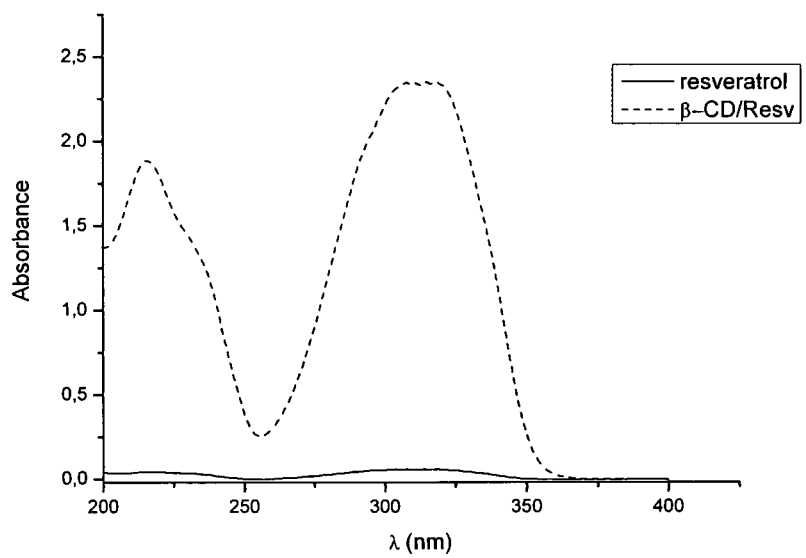
FIG. 1 presents ultraviolet spectra of trans-resveratrol (continuous line) and β-CD/Res complex (discontinuous line) in water.

The present invention overcomes several difficulties in the art, by providing a process for the substantially increasing the solubility of a resveratrol compound, preferably trans-resveratrol, to make its use more feasible. The product of such process is a cyclodextrin/resveratrol crystalline chemical complex, preferably β-cyclodextrin/trans-resveratrol complex, with high level of purity, useful as active component in medicines and/or functional foods.

The process of the present invention basically comprises the following steps: (i) dissolution of appropriate cyclodextrin in water, in a concentration equivalent to the saturation limit, with heating from 50 to 80° C. for a sufficient time to complete its dissolution; (ii) adding, to the resulting solution, an water miscible and physiologically acceptable organic solvent to an organic solvent:water ratio ranging from 1:1 to 1:5; (iii) adding, to the mixture resulting from stage (ii), a solution of a resveratrol compound diluted in an water miscible and physiologically acceptable organic solvent, and heating the resulting mixture at a temperature ranging from 50 to 80° C. for a sufficient time to complete its dissolution, preferably for a time in the range of 60 to 180 seconds; (iv) cooling slowly the solution resulting from stage (iii) until precipitation of crystals from the complex of resveratrol/cyclodextrin compound, preferably to a temperature below room temperature; and (v) separating the crystals of said complex of resveratrol/cyclodextrin compound, preferably by filtration under reduced pressure. Preferably, cyclodextrin concentration in step (i) solution ranges from 20 to 60 mM, more preferably, from 40 to 50 mM. In step (ii), preferably the addition of said water miscible and physiologically acceptable organic solvent is carried out with heating at a temperature from 50 to 80° C., for 60 to 180 seconds. The concentration of said resveratrol compound in said solution ranges from 20 to 80 mM, being preferable from 40 to 50 mM. The solution cooling in stage (iv) is gradually and slowly carried out to a preferably temperature from 10 to 20° C., and more preferably to a temperature from 13 to 17° C., being said solution kept under rest at this temperature until the substantial precipitation of the complex of resveratrol/cyclodextrin compound. Said water miscible and physiologically acceptable organic solvent can be any organic solvent in which said resveratrol compound is soluble, and it can be selected from a group comprising ethanol, acetone, DMSO, and acetic acid; with ethanol being preferable.

Although, according to the present invention, the use of resveratrol, and more preferably of trans-resveratrol, is preferred in the preparation of the invention complex, those skilled in the art will also identify that the process of solubility increase of the invention can be applied to resveratrol derivatives, such as its methylated and/or acetylated derivatives. Methylated derivatives can be: trans-3,5-dimethoxy-4'-hydroxy-stilbene, trans-3,5,4'-trimethoxy-stilbene and trans-3,5-hydroxy-4'-methoxy-stilbene, described below.

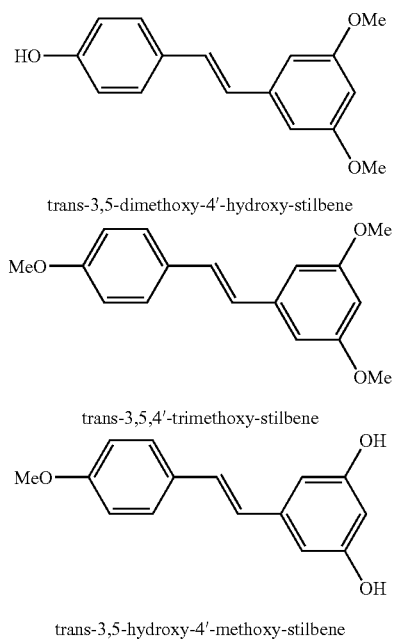

trans-3,5-dimethoxy-4'-hydroxy-stilbene trans-3,5,4'-trimethoxy-stilbene trans-3,5-hydroxy-4'-methoxy-stilbene Acetylated derivatives can be: trans-3,5-diacetyl-4'-hydroxy-stilbene, trans-3,5,4'-triacetyl-stilbene and trans-3,5-hydroxy-4'-acetyl-stilbene, described below.

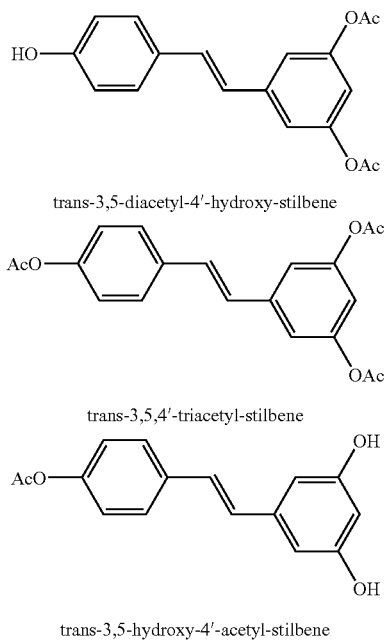

trans-3,5-diacetyl-4'-hydroxy-stilbene trans-3,5,4'-triacetyl-stilbene trans-3,5-hydroxy-4'-acetyl-stilbene In the same way, although according to the invention, β-cyclodextrin is preferred to the complexation of resveratrol or its derivatives, those skilled in the art will also deduct that the process of solubility increase of the invention can be carried out by the complexation with other cyclodextrins, such as, α-cyclodextrin (α-CD), γ-cyclodextrin (γ-CD), hydroxyethyl-β-CD, hydroxypropyl-β-CD, sulfobutyl ether β-CD, methyl-β-CD, dimethyl-β-CD, random dimethylated β-CD, random methylated β-CD, carboxymethyl-β-CD, carboxymethyl ethyl-β-CD, diethyl-β-CD, tri-O-methyl-β-CD, tri-O-ethyl-β-CD, tri-O-butyryl-β-CD, tri-O-valeryl-β-CD, di-O-hexanoyl-β-CD, glucosyl-β-CD, maltosyl-β-CD, and 2-hydroxy-3-trimethyl-aminopropyl-β-CD.

The complex of resveratrol and cyclodextrin compound of the invention obtained by complexation of the invention presents surprisingly improved properties in comparison to the state of the art, having as main characteristics its high water solubility, that is, the solubility of said complex of the invention is at least 100 times higher than the solubility of the non-complexed resveratrol compound, as well as its high purity, ranging from 91 to 98%. Other important characteristic of the complex of resveratrol/cyclodextrin compound is its crystalline form simultaneously to its high water solubility.

As it was shown, there are several differences between the process of the invention and those known by the state of the technique represented by documents WO 06/127987, WO 06/105403 and U.S. Pat. No. 6,884,885, and by Bertacche et al, 2006. The process of the invention starts from a cyclodextrin solution with concentration close to saturation, while the teachings of the state of the technique use much less concentrated initial solutions of cyclodextrin, except for the process described in U.S. Pat. No. 6,884,885. However, in this process neither water solubility nor purity of the complex is mentioned. Furthermore, in U.S. Pat. No. 6,884,885 process, the cooling stage of reaction medium to precipitate the complex is carried out under stirring until room temperature, not considering thermodynamic balance to avoid dragging non-complexed reagents and, therefore, not considering separation of the complex with high purity level. This difference is fundamental in the complexation process of the invention, because when resveratrol compound is added to a small amount of organic solvent (for example, ethanol, with sequential addition of solvent), said compound is thermodynamically forced to form the complex with cyclodextrin. In other words, resveratrol inclusion in cyclodextrin is more effective, resulting in an important difference of solubility of this complex in relation to the processes of the state of the technique. The excellence of the invention process becomes more evident when the use of beta-cyclodextrin, a crystalline cyclodextrin mentioned in the state of the technique as less soluble in the formation of the complex of resveratrol compound, provides an unprecedent water solubility enhancement of the resulting complex, when compared to the solubility of known resveratrol/cyclodextrin complexes. Consequently, the limitations pointed out in documents of the state of the technique, in that significant solubility enhancement could only be obtained by using modified cyclodextrins, do not occur in the process of the invention, mainly because the use of a β-cyclodextrin, a cyclodextrin previously considered as inappropriate for this purpose, since it surprisingly provides a substantial increase on the solubility in the conditions of the invention. Substantially different results in terms of solubility are better visualized in Table 1.

TABLE 1

Comparison between invention process and the closest state of the technique

| Features | WO 06/127987 WO 06/105403 | U.S. Pat. No. 6,884,885 | Bertacche et al, 2006 | Present invention |
|---|---|---|---|---|
| Initial Concentration of cyclodextrin solution | No regard | At least 15% (p/p) | No regard | In the limit of cyclodextrin saturation |
| Cyclodextrin and resveratrol rate | 1:0.02 | 1:1 to 10:1 | 1:1 | Preferably 1:1 |
| Organic solvent (e.g., ethanol) and water rate | 1:1 | Only water | 1:1 | 1.5:5 |
| Successive addition of solvent | No | Only water | No | Yes |
| Heating time | No | No mention | 90 s | 360 s |
| Solvent evaporation | Yes | No | Yes | No |
| Cristallization | No | Yes | No | Yes |
| Solubility increase | 20 times | No mention | 20 times | 100 times |
| Complex purity | No mention | No mention | No mention | 91-98% |

In other aspect of the invention, high purity and solubility of said modified active principle, as well as its obtainment from different and/or new plant sources, provides its advantageous use in the formulation of nutraceutical compositions, in this invention meaning those pharmaceutical compositions and/or alimentary compositions having the active principle obtained according to the invention. The resveratrol and cyclodextrin complex of the invention, when included in nutraceutical compositions, provides antioxidant, anti-inflammatory, antiviral, antidiabetics, cardioprotective, neuroprotective, chemoprotective action, besides protecting against infections and ischemia, reducing obesity, and preventing aging.

To the purposes of this invention, "pharmaceutical or nutraceutical compositions" shall mean all and any composition having an active principle, with prophylactic, palliative and/or curative aims, and a pharmaceutically acceptable vehicle/carrier, said composition acting to keep and/or recover homeostasis, enabling oral, topical, parenteral, enteral and/or intrathecal administration. The expression "nutraceutically acceptable" is here employed to refer to compounds, materials, compositions, and/or doses that are, inside medicine/nutrition field, appropriate to use in touch with human and animal tissues without excessive toxicity, irritation, allergic response, or other proportionate problem or complication, with a reasonable risk-benefit ratio. The compounds of the present invention can be administered in oral dose, such as tablets, capsules (each one includes sustained release or release time formulations), pills, powders, granules, elixirs, dyes, suspensions, syrups, and emulsions. They can also be administered by infusion and intraperitoneal, subcutaneous, or intramuscular injection, all of them using known doses to those ordinarily skilled in pharmaceutical/nutraceutical art. They can be administered alone, but in general they are administered with a pharmaceutically or nutraceutically acceptable vehicle selected from the basis of chosen administration route and from standard pharmaceutical/nutraceutical practice. Dose regimen for the compounds of the present invention, of course, will vary according to the known factors, such as pharmacodynamic characteristics of a specific agent and administration route and modality, race, age, gender, health, medical condition, and receptor weight, symptom nature and extension; type of simultaneous treatment; treatment frequency; administration route, patient/user's hepatic and renal function, and aimed effect. For example, oral solid forms preferably have, in addition to active principle, a pharmaceutically or nutraceutically acceptable vehicle comprising one or more diluents, such as, lactose, dextrose, saccharose, cellulose, corn starch or potato starch; one or more lubricants, such as, silica, powder, stearic acid, magnesium or calcium stearate, or polyethylene glycols; one or more binding agents (agglutinants), such as, starches, mucilage, gelatin, methylcellulose, carboxymethylcellulose or polyvinyl pyrrolidone; one or more disaggregating agents, such as, starch, alginic acid, alginates or sodium starch glycolates; effervescent mixtures; dyes; sugary agents; one or more humectant agents, such as, lecithin, polysorbate, laurylsulphate; and pharmacologically/nutraceutically inactive and non-toxic substances generally used in pharmaceutical/nutraceutical formulations and broadly known by pharmacotechnical workers. The compositions of the invention can be manufactured in a known way, for example, by means of mixture, granulation, tablet press, sugarcoating, or processes of film coating. Liquid nutraceutical forms for oral administration can be, for example, syrups, emulsions, or suspensions. Syrups can have a pharmaceutically or nutraceutically acceptable vehicle, such as, saccharose or saccharose with glycerin and/or manita (mannitol) and/or sorbitol. Suspensions and emulsion can have a pharmaceutically or nutraceutically acceptable vehicle, such as, a natural gum, agar, sodium alginate, pectin, methylcellulose, carboxymethylcellulose or polyvinilic alcohol. The forms intended for intramuscular injections can have, additionally to active principle, a pharmaceutically or nutraceutically acceptable vehicle, such as, sterile water, olive oil, ethyl oleate, propylene glycol and, an appropriate amount of lidocaine hydrochloride. In the present invention, oral forms are preferred.

The following examples illustrate, but do not limit, the preferred embodiments of the invention. Improved processes to obtain beta-cyclodextrin/trans-resveratrol compound in a ratio of 1:1 are shown. The isolation of the complex was carried out by cooling, and aqueous medium solubility of trans-resveratrol was increased about 100 times.

Example 1

Obtainment of Beta-Cyclodextrin (β-CD) and Trans-Resveratrol Complex

Trans-resveratrol used was that obtained by the process describe in patent application PI 0700152-5, by the same inventor, or bought from Sigma-Aldrich. Beta-cyclodextrin (CAVAMAX W& Pharma) was bought from ISP Technologies, Inc.

Figure 6:
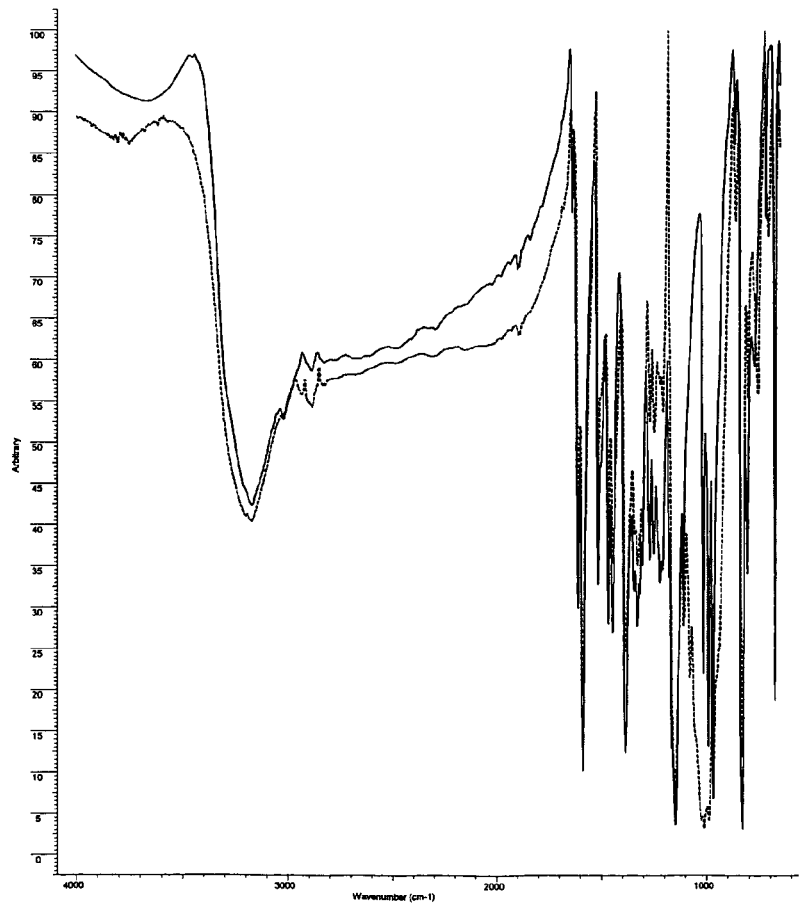
FIG. 6 presents FTIR-ATR spectra of trans-resveratrol (continuous line) and β-CD/Res complex (discontinuous line).

Fifty g of β-CD (44 mM) and 1000 mL of distilled water were put in a 5000 mL beaker. The mixture was heated to a temperature ranging 60-70° C. in a microwave oven, for 90 seconds. Soon after, 100 to 200 mL of ethanol 96% were added, and the mixture was heated again twice to a temperature ranging 60-70° C. in a microwave oven, for 90 seconds. To the resulting solution, 10 g of trans-resveratrol (44 mM) diluted in 50-100 mL of ethanol 96% were added. The mixture was heated once or twice to a temperature ranging 60-70° C. in a microwave oven, for 90 seconds. The resulting solution was slowly cooled at 15° C. and left at this temperature up to 24 hours. The crystals formed from trans-resveratrol/β-cyclodextrin (β-CD/Res) complex were collected by filtration under reduced pressure, and dried in a vacuum oven at 60° C., resulting in 14.5-28 g of the invention complex with purity from 91 to 98% and a yield around 56%. Besides, filtrate (resulting solution) was freeze dried, providing 45.5-31.5 g of solid material having non-reacted components and other complexes (FIGS. 1 and 6).

Example 2

Water Solubility of Beta-Cyclodextrin (β-CD) and Trans-Resveratrol Complex

Figure 2:
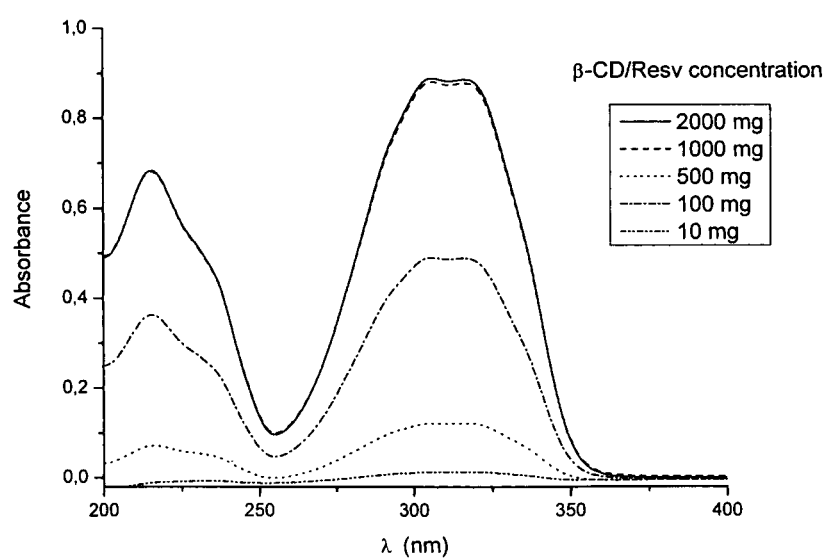
FIG. 2 shows ultraviolet spectra in different concentrations of β-CD/Res complex in water.
Figure 3:
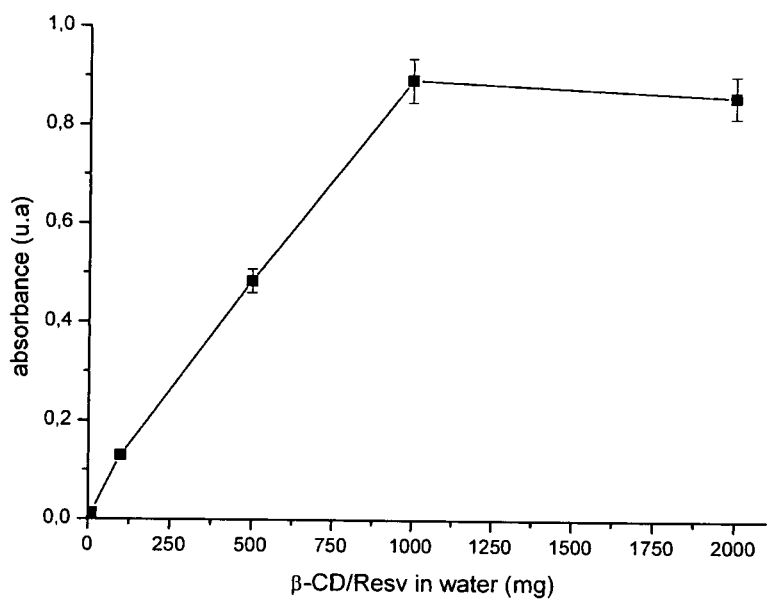
FIG. 3 presents a chart of the different concentrations of β-CD/Res complex in water in $\lambda$=306 nm.

Ten mg, 100 mg, 500 mg, 1000 mg and 2000 mg of β-CD/Res complex were put in 100 mL volumetric flasks and water was added until completing their volume. The solutions stayed at ultrasound for 60 minutes. Then samples were centrifuged and filtered in a 0.45 μm pore diameter cellulose acetate membrane. Twenty μL portions of the samples were diluted 2000 times and their absorbances were measured by a UV-VIS spectrophotometer (FIG. 2). It was noticed that system saturation happens from 1000 mg of β-CD/Res (FIG. 3). The concentration of trans-resveratrol in 1000 mg and 2000 mg β-CD/Res sample concentrations was determined by High-Performance Liquid Chromatography (HPLC). For quantification, an external calibration curve was used, with trans-resveratrol concentrations ranging from 0.10 a 200.0 mg.L$^{-1}$. HPLC was carried out in isocratic elution (flow of 1.0 mL min$^{-1}$), with an aqueous solution of 25% acetonitrile, pH 3.0, adjusted with $H_3PO_4$. The chromatograph was equipped with UV-VIS detector and a $C_{18}$ column, 5 μm 250×4.6 mm. Sample portions were diluted 1000 times with eluent, and 20 μL were injected and detected in 306 nm. The concentrations of trans-resveratrol of the 1000 mg sample of β-CD/Res complex were 3010±62 mg.L$^{-1}$ and of the 2000 mg sample of βCD/Res complex were 2960.5±53 mg.L$^{-1}$. It was also determined water solubility of trans-resveratrol by the procedure described above, and the result was 27.5±0.45 mg.L$^{-1}$. All analyses were carried out in quintuplicate.

TABLE 2

Relative solubility of different preparations having resveratrol and beta-cyclodextrin.

| Property | Pure resveratrol | WO 06/127987 (US 06/0292099) WO 06/105403 | Bertacche et al, 2006 (article) | Present invention |
|---|---|---|---|---|
| Solubility | 27.5 mg L$^{-1}$ | 550 mg L$^{-1}$ (Method equivalent to Bertacche et al) | 550 mg L$^{-1}$ | 3010 mg L$^{-1}$ |

As it can be noticed in Table 1, the solubility increase of the invention complex is greater than 400% (5.47 times) in comparison to the best result available in prior art and greater than 9000% (100 times) in isolate comparison to resveratrol. Such results are worthwhile for several uses of resveratrol, mainly those aimed by the present invention, since resveratrol low solubility is a problem for its preparation/galenic pharmacy and for its bioavailability.

Example 3

Solubility of Beta-Cyclodextrin (β-CD)/Trans-Resveratrol Complex in Grape Juice

Figure 4:
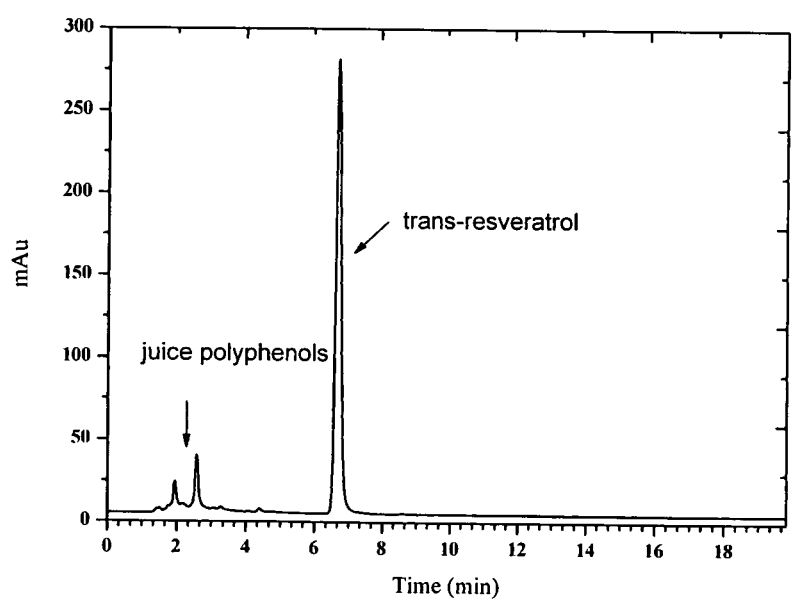
FIG. 4 presents a chromatogram of saturate grape juice of β-CD/Res complex.

One thousand mg of β-CD/Res complex were added to 100 mL of grape juice. The solutions stayed at ultrasound for 60 minutes. Then samples were centrifuged and filtered in a 0.45 μm pore diameter cellulose acetate membrane. The concentration of trans-resveratrol in juice with β-CD/Res was determined by High-Performance Liquid Chromatography (HPLC). For quantification, an external calibration curve was used, with trans-resveratrol concentrations ranging from 0.10 a 200.0 mg.L$^{-1}$. HPLC was carried out in isocratic elution (flow of 1.0 mL min$^{-1}$), with an aqueous solution of 25% acetonitrile, pH 3.0, adjusted with $H_3PO_4$. The chromatograph was equipped with UV-VIS detector and a $C_{18}$ column, 5 μm 250×4.6 mm. A juice portion having β-CD/Res was diluted 1000 times with eluent, and 20 μL were injected and detected in 306 nm. The concentration found was 2650±51 mg.L$^{-1}$ (FIG. 4). All analyses were carried out in quintuplicate.

Example 4

Figure 5:
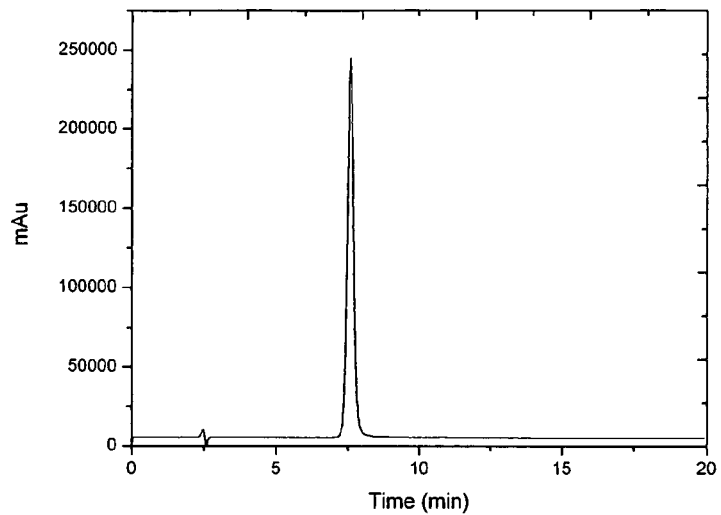
FIG. 5 presents a chromatogram of saturate soybean juice of β-CD/Res complex.

Solubility of Beta-Cyclodextrin (β-CD) and Trans-Resveratrol Complex in Soybean Juice One thousand mg of β-CD/Res invention complex were added to 50 mL of soybean juice of different flavors (natural, orange, grape, peach, pineapple, etc). The suspension stayed at ultrasound for 60 minutes. Then sample was centrifuged at 10.000 rpm and filtered in a 0.45 μm pore diameter cellulose acetate membrane. The concentration of trans-resveratrol in juice with β-CD/Res was determined by High-Performance Liquid Chromatography (HPLC). For quantification, an external calibration curve was used, with trans-resveratrol concentrations ranging from 0.10 a 200.0 mg.L$^{-1}$. HPLC was carried out in isocratic elution (flow of 0.9 mL min$^{-1}$), with an aqueous solution of 25% acetonitrile, pH 3.0, adjusted with $H_3PO_4$. The chromatograph was equipped with UV-VIS detector and a $C_{18}$ column, 5 μm 250×4.6 mm. A juice portion having β-CD/Res was diluted 100 times with eluent, and 20 μL were injected and detected in 306 nm. The concentration found was 2380±71 mg.L$^{-1}$ (FIG. 5). All analyses were carried out in quintuplicate.

Those skilled in the art will immediately appreciate the important benefits brought by the use of the present invention, such as products having trans-resveratrol/cyclodextrin complex with high water solubility level, as well as pharmaceutical, nutraceutical and/or phytoherapic compositions comprising them.

It is to be expressly understood that variations in the way of performing the inventive concept here described are to be deed within the scope of the invention and the claims attached.

The invention claimed is:

1. A resveratrol and cyclodextrin compound complex produced from a process comprising the steps of:
   a) completely homogenizing β-cyclodextrin in water with heating from 50 to 80° C., up to a β-cyclodextrin concentration lower than or equal to 60 mM;
   b) adding, to the solution resulting from step (a), a water miscible and physiologically acceptable organic solvent, up to an organic solvent:water ratio ranging from 1:1 to 1:5;
   c) adding, to the mixture resulting from step (b), a solution of a trans-resveratrol compound diluted in a water miscible and physiologically acceptable organic solvent, and heating the resulting mixture at a temperature range from 50 to 80° C.;
   d) cooling slowly the solution resulting from step (c) until precipitation from the mixture of crystals of the resveratrol and cyclodextrin compound complex; and
   e) separating out the crystals of the resveratrol and cyclodextrin compound complex, wherein the resveratrol and cyclodextrin compound complex is in a solid crystalline form and has a solubility of about 3010 mg/L in water.

2. The resveratrol and cyclodextrin compound complex according to claim 1, wherein said solvent is selected from the group consisting of ethanol, acetone, DMSO, and acetic acid.

3. The resveratrol and cyclodextrin compound complex according to claim 2, wherein said water miscible and physiologically acceptable organic solvent is ethanol.

4. The resveratrol and cyclodextrin compound complex according to claim 1, wherein the concentration of said β-cyclodextrin of the solution in step (a) ranges from 20 to 60 mM.

5. The resveratrol and cyclodextrin compound complex according to claim 4, wherein the concentration of said β-cyclodextrin ranges from 40 to 50 mM.

6. The resveratrol and cyclodextrin compound complex according to claim 1, wherein in step (b), the addition of said water miscible and physiologically acceptable organic solvent is carried out with heating at a temperature from 50 to 80° C., for 60 to 180 seconds.

7. The resveratrol and cyclodextrin compound complex according to claim 1, wherein the concentration of said trans-resveratrol compound of said solution in step (c) ranges from 20 to 80 mM.

8. The resveratrol and cyclodextrin compound complex according to claim 7, wherein the concentration of said trans-resveratrol compound ranges from 40 to 50 mM.

9. The resveratrol and cyclodextrin compound complex according to claim 1, wherein the cooling of the solution in step (d) is carried out gradually and slowly to a temperature from 10 to 20° C., said solution being kept at rest in this temperature for precipitation of the formed complex.

10. The resveratrol and cyclodextrin compound complex according to claim 1, wherein the cooling of the solution in step (d) is carried out gradually and slowly to a temperature from 13 to 17° C., said solution being kept at rest in this temperature for precipitation of the formed complex.

11. The resveratrol and cyclodextrin compound complex according to claim 1, wherein the separation of the crystals of said resveratrol and cyclodextrin compound complex is carried out by filtration under reduced pressure.

12. The resveratrol and cyclodextrin compound complex according to claim 1, wherein the crystals of said resveratrol and cyclodextrin compound complex resulting from step (e) are subjected to drying.

13. A nutraceutical composition comprising as active and/or functional component a trans-resveratrol and β-cyclodextrin compound complex in a solid crystalline form, and a nutraceutically acceptable vehicle,
wherein said trans-resveratrol and β-cyclodextrin compound complex is produced from a process comprising the steps of:
a) completely homogenizing β-cyclodextrin in water with heating from 50 to 80° C., up to a β-cyclodextrin concentration lower than or equal to 60 mM;
b) adding, to the solution resulting from step (a), a water miscible and physiologically acceptable organic solvent, up to an organic solvent:water ratio ranging from 1:1 to 1:5;
c) adding, to the mixture resulting from step (b), a solution of a trans-resveratrol compound diluted in a water miscible and physiologically acceptable organic solvent, and heating the resulting mixture at a temperature range from 50 to 80° C.;
d) cooling slowly the solution resulting from step (c) until precipitation from the mixture of crystals of the resveratrol and cyclodextrin compound complex; and
e) separating out the crystals of the resveratrol and cyclodextrin compound complex,
wherein the resveratrol and cyclodextrin compound complex is in a solid crystalline form and has a solubility of about 3010 mg/L in water.

14. A pharmaceutical composition comprising as active and/or functional component a trans-resveratrol and β-cyclodextrin compound complex in a solid crystalline form, and a pharmaceutically acceptable vehicle,
wherein said trans-resveratrol and β-cyclodextrin compound complex is produced from a process comprising the steps of:
a) completely homogenizing β-cyclodextrin in water with heating from 50 to 80° C., up to a β-cyclodextrin concentration lower than or equal to 60 mM;
b) adding, to the solution resulting from step (a), a water miscible and physiologically acceptable organic solvent, up to an organic solvent:water ratio ranging from 1:1 to 1:5;
c) adding, to the mixture resulting from step (b), a solution of a trans-resveratrol compound diluted in a water miscible and physiologically acceptable organic solvent, and heating the resulting mixture at a temperature range from 50 to 80° C.;
d) cooling slowly the solution resulting from step (c) until precipitation from the mixture of crystals of the resveratrol and cyclodextrin compound complex; and
e) separating out the crystals of the resveratrol and cyclodextrin compound complex,
wherein the resveratrol and cyclodextrin compound complex is in a solid crystalline form and has a solubility of about 3010mg/L in water.

* * * * *